United States Patent
Arent (12) 
(10) Patent No.: US 6,358,202 B1
(45) Date of Patent: Mar. 19, 2002

(54) NETWORK FOR IMPLANTED COMPUTER DEVICES

(75) Inventor: Michael Arent, Albany, CA (US)

(73) Assignee: Sun Microsystems, Inc., Palo Alto, CA (US)

( * ) Notice: Subject to any disclaimer, the term of this patent is extended or adjusted under 35 U.S.C. 154(b) by 0 days.

(21) Appl. No.: 09/483,214

(22) Filed: Jan. 14, 2000

Related U.S. Application Data
(60) Provisional application No. 60/117,116, filed on Jan. 25, 1999.

(51) Int. Cl.$^7$ ................................................ A61B 5/00
(52) U.S. Cl. .............................. 600/300; 607/2; 607/60; 607/32; 128/920
(58) Field of Search ............................... 607/2, 1, 3, 4, 607/5, 9, 27, 30, 31, 32, 59, 60, 17–24; 600/300, 301, 309, 364, 361, 509, 483, 504, 485, 549, 561, 322, 323; 128/903, 904, 920

(56) References Cited

U.S. PATENT DOCUMENTS

| | | | |
|---|---|---|---|
| 4,886,064 A | * 12/1989 | Strandberg | 607/18 |
| 4,987,897 A | * 1/1991 | Funke | 607/32 |
| 5,549,659 A | 8/1996 | Johansen et al. | |
| 5,733,313 A | 3/1998 | Barreras, Sr. et al. | |
| 5,814,089 A | 9/1998 | Stokes et al. | |
| 6,083,248 A | * 7/2000 | Thompson | 607/30 |
| 6,296,698 B1 | * 9/2001 | Duffin et al. | 607/32 |

FOREIGN PATENT DOCUMENTS

| | | |
|---|---|---|
| EP | 0362611 A1 | 4/1990 |
| WO | WO 98/56459 | 12/1998 |

OTHER PUBLICATIONS

Jones et al., A Protocol for Automatic Sensor Detection and Identification in a Wireless Biodevice Network, Dec. 6, 1998, Eleventh IEEE Symposium on Computer–Based Medical Systems.
Fernald et al., A System Architecture for Intelligent Implantable Biotelemetry Instruments, 1989, IEEE Engineering in Medicine and Biology Society 11$^{th}$ Annual International Conference.
Kevin Warwick, CYBORG 1.0, Feb. 2000, Wired.

* cited by examiner

Primary Examiner—Kennedy Schaetzle
(74) Attorney, Agent, or Firm—Beyer Weaver & Thomas, LLP (57) ABSTRACT

A network device that can be implanted in a subject is described. The device is configured to communicate over a computer network. In one embodiment, the device of the invention includes an internal interface in physiological communication with the subject. The internal interface is coupled with, and configured to send signals to, a processor. The processor is configured to receive and process the signals, and is further configured to communicate over a computer network with another such device. Such devices can be used to monitor and communicate information regarding a host's physiological status, monitor and/or control artificial organs and prosthetic devices, and/or dispense medication.

28 Claims, 8 Drawing Sheets

NETWORK FOR IMPLANTED COMPUTER DEVICES

This application claims the benefit of U.S. Provisional Application No. 60/117,116 filed on Jan. 25, 1999, the disclosure of which is incorporated herein by reference.

BACKGROUND OF THE INVENTION

1. Field of the Invention

The present invention relates to the areas of computer networks and networked devices. More specifically, the present invention relates to devices configured to be implanted in a subject and create a communications network within the subject. The present invention has applications in the areas of computer science, biology, and medicine.

2. The Related Art

Individuals suffering from a wide variety of illnesses and physical disabilities require constant or frequent monitoring and/or medical intervention to survive, or at least maintain a relatively normal lifestyle. Examples of such diseases include heart disease, cancer, and Parkinson's disease. Treatment of heart disease can require heart rate and/or blood pressure monitoring to detect dangerous physiological states as well as the administration of drugs to reduce or eliminate those states. Often medication or other intervention (e.g., defibrillation) must be provided immediately for best effect. Other diseases, including cancer and Parkinson's disease, often require long-term—or perpetual—delivery of medication. In some cases, delivery is optimized by providing the medication during certain time periods.

Advances in the miniaturization of electronics and mechanical devices have provided various implantable devices to meet these needs. Internal heart monitors and pacemakers can provide constant detection and intervention to treat heart disease. Implanted drug delivery devices can provide programmed delivery of medications. Often these devices include on-board computers, and, in some cases, these computers can communicate with external devices to exchange data and instructions (see, e.g., Morgan and Richards 1995; Prutchi and Paul 1998; Snell and Levin 1998).

However, implanted medical devices are not designed to communicate with other such devices. Rather, device designs attempt to include both monitoring and intervention functions (e.g., drug delivery or stimulus) in a single unit. This design philosophy increases the complexity of the implanted device, thereby increasing the cost of the device and reducing its reliability. In addition, the use of single devices reduces or eliminates the ability to efficiently gather and aggregate physiological data from various points in the body. Such widespread data gathering can be useful given the body's highly coupled biochemical systems. For example, some disorders (for example, endocrine disorders) could be better addressed by monitoring and treating the body at disparate locations. Present implanted medical device designs preclude such options.

Therefore, it would be advantageous to provide implanted medical devices that can be linked in a network so that separate, specialized implanted devices can perform monitoring and intervention functions. Moreover, it would be advantageous to provide networked implanted devices to collect and communicate data on the holistic physiological state of a patient at one or more remote internal locations. These advantages and more are provided by the present invention.

SUMMARY OF THE INVENTION

The present invention provides methods, devices, and software to implement networks of devices internal and/or external to a host. Such networks can address the shortcomings described above in addition to provide additional information about the host. Examples of such additional information include, without limitation, the host's location and/or local external environment. Thus, the present invention will be seen to address important needs in gathering medical and biological data.

In a first aspect, the present invention provides a network device that can be implanted in a subject. The device of the invention is configured to communicate over a computer network. In one embodiment, the device of the invention includes an internal interface in physiological communication with the subject. The internal interface is coupled with, and configured to send signals to, a processor. The processor is configured to receive and process the signals, and is further configured to communicate over a computer network with another such device. The processor is further coupled with a computer memory for storing data and instructions, an external interface for sending and receiving signals over the computer network, and a power source.

In a more particular embodiment of the device of the invention, the internal interface comprises a sensor. The sensor can include an antibody detection component. The antibody detection component can be configured to include antibodies directed to tumor-specific antigens, a virus or viral product, a bacterium or bacterial product, or a metabolite of the subject. The sensor can also be configured to measure a physiological parameter of the subject. Examples of relevant physiological parameters include, without limitation, heart rate, blood oxygen concentration, blood flow rate, temperature, and blood pH.

In one embodiment, the device is implanted at an internal location in the subject. Alternatively, the device can be implanted transdermally such that a portion of the device (e.g., an interface) is exposed through the subject's skin. The device can also be mounted on the skin of the subject, or worn by the subject. The devices can be configured to communicate with sources and computer networks external to, and/or remote from, the subject.

In another aspect, the present invention provides a method for monitoring the physiological condition of a subject. In one embodiment, a device of the invention is implanted in a subject. Communication is established with the subject, and at least one physiological parameter of the subject is determined using the device. The measured parameter is communicated using the device over a computer network. Communication can include sending a signal to another implanted device or to an external receiver. The device can also receive signals from a second such device. In one embodiment, a therapeutic substance is dispensed under control of such a second device.

In another embodiment of this second aspect of the invention, a determination is made whether a signal should be sent to such second device and sending such signal if a positive determination is made. In still another embodiment, a signal is received from a networked device by the implanted device. The signal is processed and a determination is made whether the signal is interpretable and, if the signal is interpretable, then determining whether an action is required. The action is executed if required.

In another embodiment, the present invention is able to monitor and/or control artificial organs such as an artificial heart, kidney, pancreas, etc., as well as monitor and/or control a prosthetic device such as an artificial limb, eye, tooth, etc.

These and other aspects and advantages will become apparent when the Description below is read in conjunction with the accompanying Drawings.

DESCRIPTION OF SOME EMBODIMENTS OF THE INVENTION

The present invention provides methods, software, and systems for implementing networks of medical devices or other implanted or externally mounted devices. Such networks can include two or more networked devices implanted within a host. The networks can also include transdermally- or externally-mounted devices as well. The networked devices can also be in communication with one or more sources or devices external to, and remote from, the host, including display devices, storage devices, and/or pharmaceutical dispensing devices. The networks can be hard-wired networks that include electrically or optically conductive materials to link the networked implanted devices. The networks can also be wireless networks that employ signals broadcast from the implanted devices. Thus, the software, methods, and systems provided herein can provide real-time monitoring of physiological functions at multiple anatomical locations in addition to control of pharmaceutical delivery to a patient. Such monitoring and control can be performed on-site at a medical facility or remotely.

Figure 1:
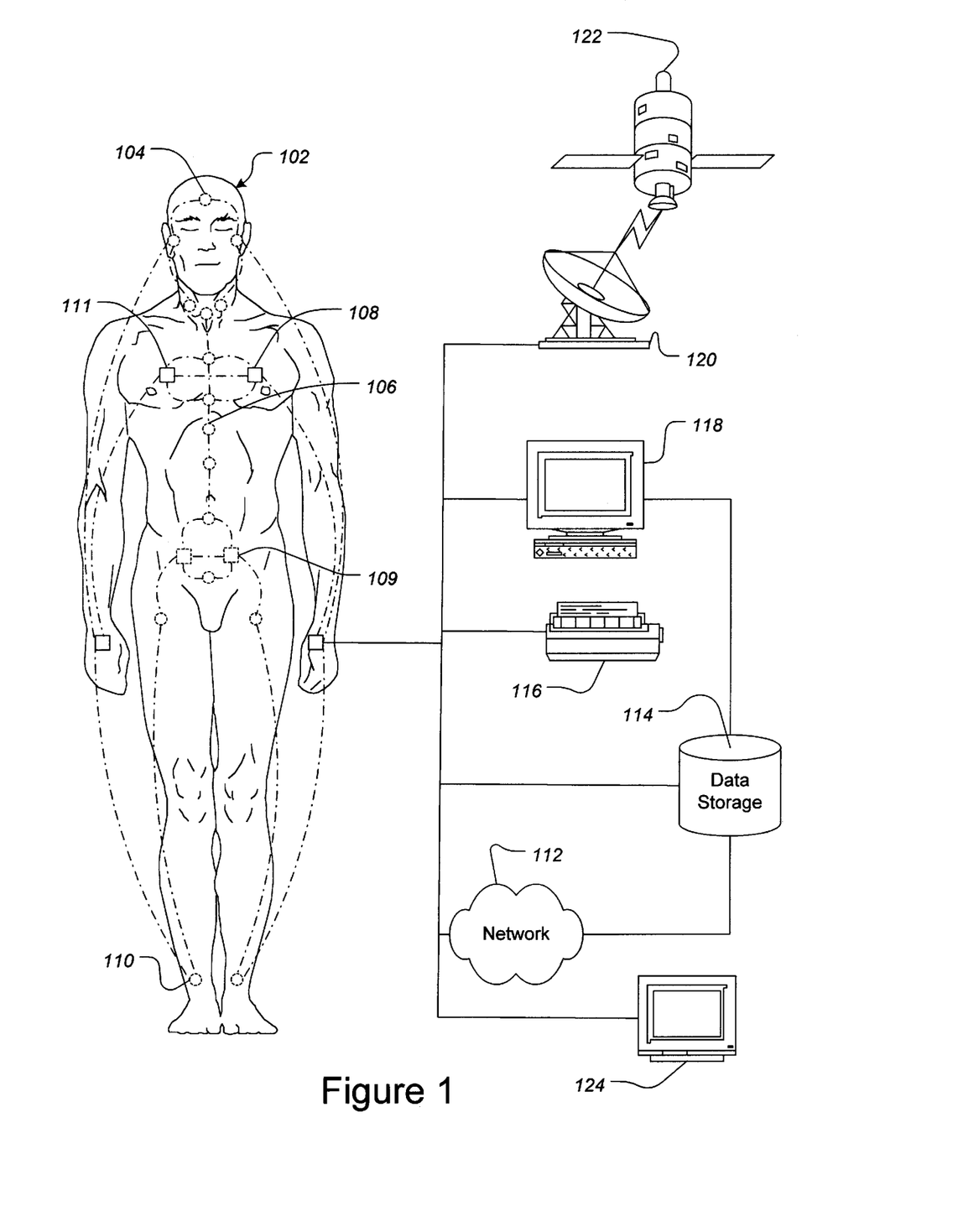
FIG. 1 illustrates a wireless network including implanted and external medical devices and sensors in addition to external communications, storage, and display devices in accordance with one embodiment of the present invention.

FIG. 1 illustrates one embodiment of a wireless network of implanted medical devices within a patient or host 102. The devices include subcutaneously implanted, networked devices 104 and 106. Such devices are defined herein as devices implanted in the body of the patient or host and are represented by circles (○). Transdermally implanted, networked devices 108 and 109 also are provided. These devices are represented by squares (□) and are defined herein as devices of the invention implanted in the body of the patient or host such that at least a portion of the device can be perceived through the skin. In addition, the devices of the invention can also be mounted externally on the host (not shown). For example, suitable devices can be worn around the waist, wrist, neck, or other appropriate anatomical location. Alternatively, the external devices can also be attached to the epidermis of the host, e.g., as a "patch". As noted above, however, the devices of the invention can be part of a "wired" network in which signals between devices are carried on a conductive wire.

In one embodiment, the subcutaneous and transdermal devices communicate data and instructions using a wireless network as indicated by the dashed lines linking the devices in the Figure. For example, device 104 communicates with device 110 and device 108 communicates with device 109. Such communication can be by direct connection between the devices (e.g., devices 108 and 111) or via intermediate devices (e.g., communication between devices 108 and 109 via device 106). The device of the internal network can further communicate by physical or wireless connection to larger networks (e.g., network 112), data storage devices 114, printers 116, workstations or other computers 118, satellite link 120 and 122, and/or monitor 124.

Each of devices 104–111 can be any implantable medical device having a configuration sufficient to perform the computational and communications functions necessary for wireless network operation. One example of the general architecture of a suitable device is provided at 200 in FIG. 2. Device 200 includes a microprocessor 202 that is coupled with a power source 204, programmable memory 206, read-only memory ("ROM") 208, random access memory ("RAM") 210, an internal interface 212, and an external interface 214. These above-described components can be provided in a single housing (shown by dashed border 216), or in one or more individual housings that include couplings sufficient to enable the connections among components 202–214 as described above.

Figure 2:
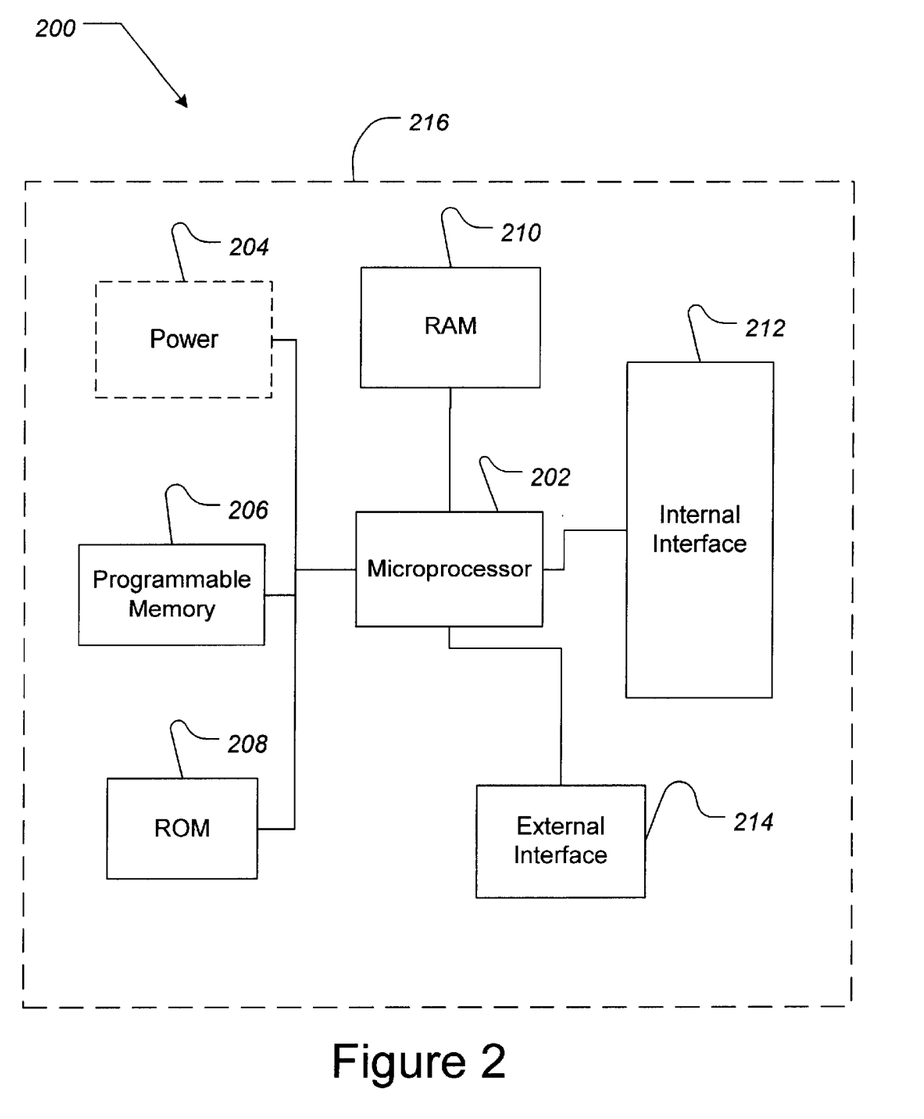
FIG. 2 illustrates a system architecture for devices configured to operate in a wireless network in accordance with one embodiment of the present invention.

Microprocessor 202 can be any data processing device configured to process data and instructions consistent with the function or functions of the device. Examples of such processors include specialty processors, such as application-specific integrated circuits ("ASICs"), or general-purpose microprocessors, such as the ARM® processor (available commercially from Advanced RISC Machines Ltd. of Cambridge, UK) or the PowerPC® processor (available commercially from Motorola of Schaumburg, Ill.). Programmable memory 206, ROM 208, and RAM 210 are of standard design and construction. Examples of such processors and memory devices are known to those having skill in the electronics and bio-electronics arts (see, e.g., Stone 1983; Martin and Chapman 1989; Ralston and Reilly 1993; Herzog 1996). More particular examples include processors known to those of skill in the computer science and electronics arts as "embedded processors". These devices are compatible with real-time operating systems as described below. Examples of suitable embedded processors include those sold under the tradenames OS-9 (from Microware of DesMoines, Iowa) and VXWORKS (from Wind River Systems of Alameda, Calif.).

Power source 204 can be any source of electrical energy sufficient to allow operation of the implanted device, such as a battery or the like. For example, the power source can include both a battery and rechargeable back-up source of electrical energy (see, e.g., Barreras and Jimenez 1998). A wide variety of these and other suitable devices will be known to those of skill in the medical device and bio-electrical engineering arts.

External Interface 214 can be any device or combination of devices configured to allow communication of the implantable device with other implanted devices and/or external devices such as those illustrated in FIG. 1. Examples of external interfaces include RF-coupled devices (see, e.g., Barreras and Jimenez 1998; Barreras and Echarri 1998), other configurations will also be familiar to those of skill in the bio-electronics arts (see, e.g., Genest 1985; Pollack 1989; Morgan and Richards 1995; Myllymäki 1997; Prutchi and Paul 1998; Snell 1998; Snell and Levin 1998). In some transdermal embodiments (e.g., device 108 of FIG. 1), the external interface will include a perceptible indicator responsive to the status of the host. Examples of visible indicators include light-emitting diodes ("LEDs") and liquid crystal diodes ("LCDs"). An audible indicator can also be implemented. Still other suitable examples will be familiar to those having skill in the medical device and bio-electrical engineering arts.

Internal interface 212 includes one or more devices configured to determine the status of one or more physiological parameters of the host. Such physiological parameters can include any quantity that can be measured by physical, chemical, or immunological means. Examples of such parameters include heart rate, blood flow velocity, blood pH, blood chemistry composition, respiration rate, body temperature, the presence of antibodies or other immunological components (e.g., compliment factors, neutrophils, and/or marcophages), the presence of antigens or antigenic determinants, the presence of hormones, enzymes, or other biochemically relevant molecules (e.g., carbohydrates, proteins, or polynucleotides). A wide variety of technologies are available to implement such detection in accordance with the present invention (see, e.g., Nappholz, Hursta et al. 1992; Hogen Esch 1994; Zurbrügg 1996; Crooks and Ricco 1998; Lauks 1998; Mitrovics, Ulmer et al. 1998; Prutchi and Paul 1998; Semancik and Cavicchi 1998; Walt 1998). In other embodiments, the internal interface is not included. For example, the device may be configured to provide a central data collection and processing point. In another example, the device is configured to provide external communication as well as data collection and processing.

Internal interface 212 may also monitor any of a variety of artificial organs such as an artificial heart, kidney, pancreas, etc., as well as monitor and/or control a prosthetic device such as an artificial limb, eye, tooth, etc.

Figure 3:
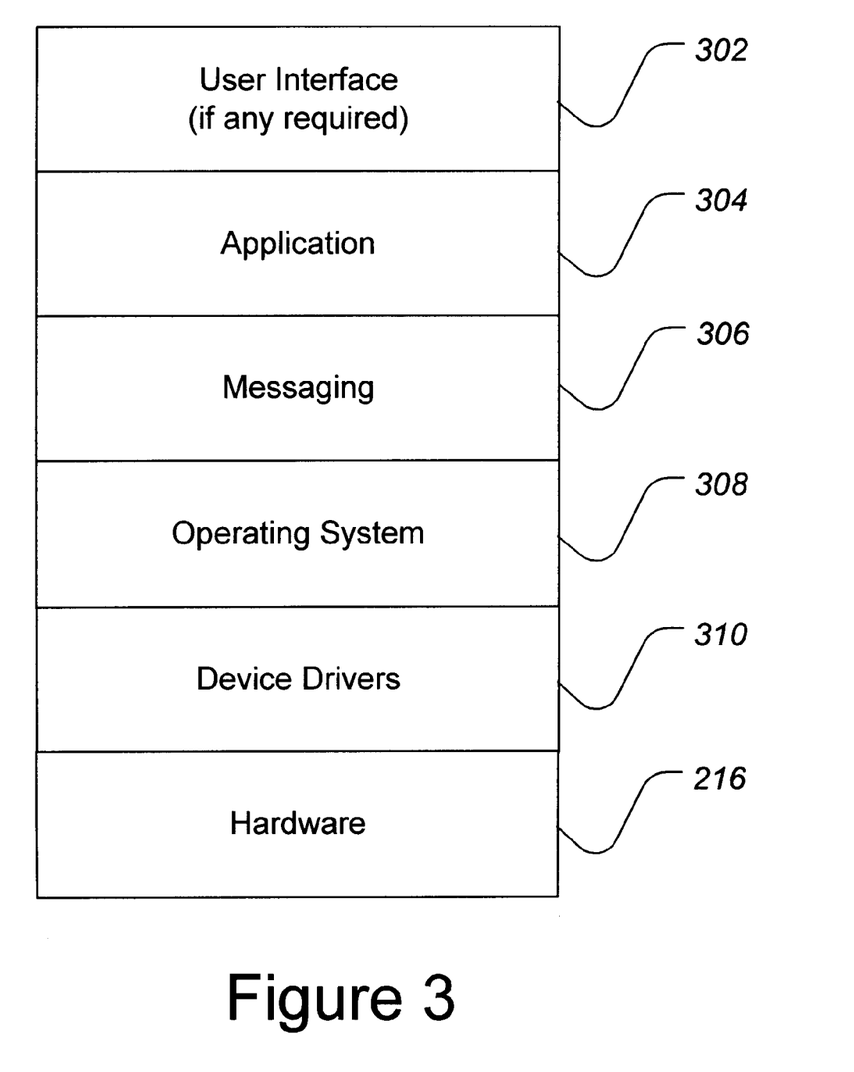
FIG. 3 illustrates a software architecture for a device configured to operate in a wireless network in accordance with one embodiment of the present invention.

FIG. 3 illustrates one embodiment of a software architecture for an implantable device of the invention. In the illustrated embodiment, a user interface ("UI") 302 is provided that is configured to allow access to the application(s), operating system and associated support software running on microprocessor as described below. In some cases, UI 302 is accessible only from external programming and configuring devices in remote communication with the device. In other cases, UI 302 includes elements that are accessible from the device itself. For example, transdermal devices can include UI elements such as buttons (physical-or soft-buttons) that can be activated by the host or caregiver to configure the implantable device.

Application layer 304 includes one or more applications configured to implement the function of the implantable device. Such applications include software configured to acquire and/or process signals received from internal interface 212 (e.g., heart rate or antigen concentration), software configured to provide communication with other networked devices (both internal and/or external). In one embodiment, application layer 304 includes software written in a device-independent programming language. In a more particular embodiment, the device-independent software is written in a language that include instructions provided as bytecodes. Such languages include the Java® programming language (available from Sun Microsystems, Inc. of Palo Alto, Calif.). The design and construction of such software and other suitable languages will be familiar to those of skill in the computer science and electronics arts (see, e.g., Campione and Walrath 1998).

Beneath Application Layer 304 is Messaging Layer 306 that handles communications between application(s) running in Application Layer 304 and other devices. Underneath Messaging Layer 306 is Operating System 308. Operating System 308 is chosen and configured to allow application(s) running on Application Layer 304 to operate on the implantable device of the invention. In one embodiment, Operating System 308 includes a real-time operating system and/or a virtual machine configured to process bytecodes used to implement applications running on the Application Layer. Various Device Drivers 310 can also be included to implement software instructions using hardware elements included with the implantable device such as devices associated with Internal Interface 212. The design and construction of such software will be familiar to those of skill in the computer science and electronics arts (see, e.g., Martin and Chapman 1989).

Figure 4:
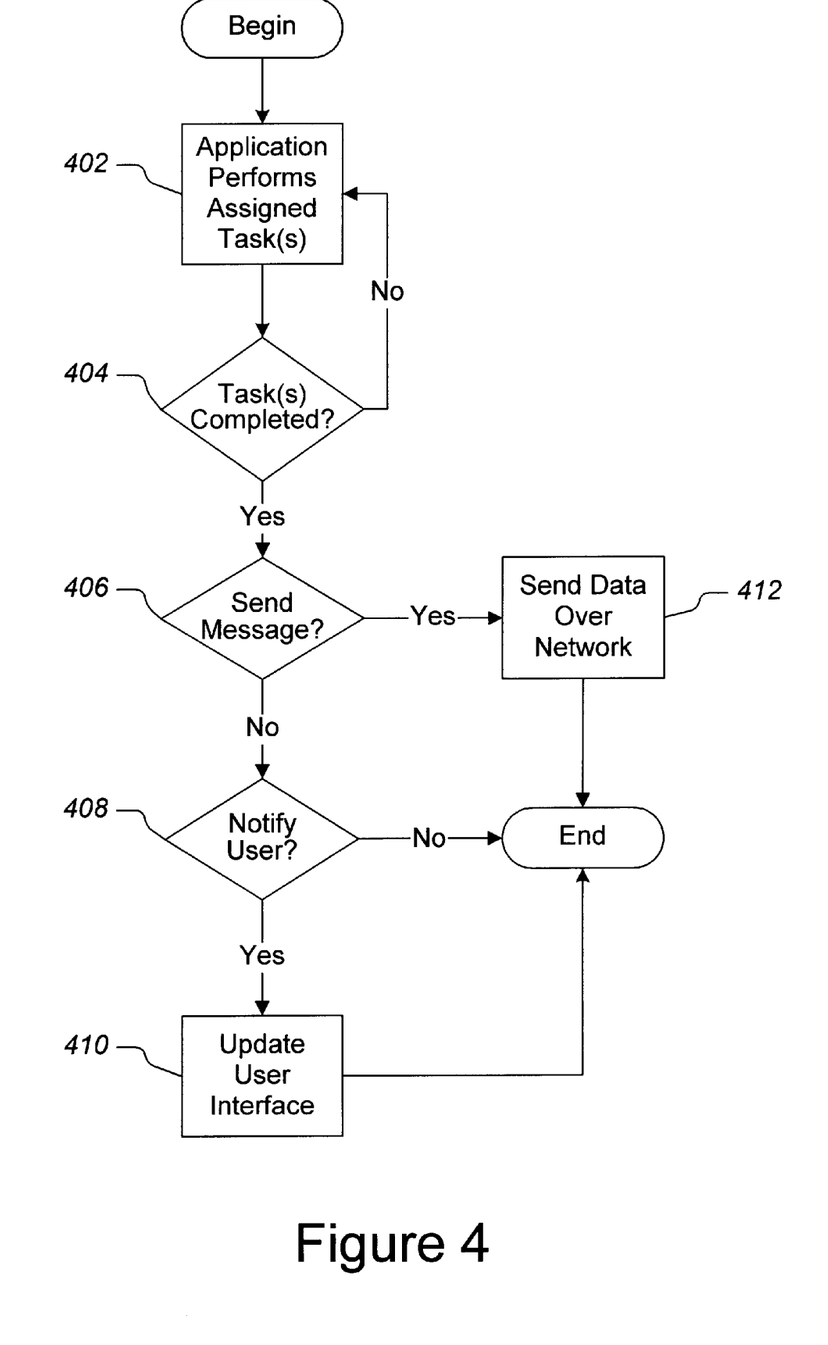
FIG. 4 is a flowchart illustrating the operation of a device configured to operate in a wireless network in accordance with one embodiment of the present invention.

One embodiment of a method of operation for an implantable device of the invention is provided in FIG. 4. Starting at step 402 the application(s) running on the application layer perform their task (e.g., processing data obtained from physiological measurements made using Interface Layer 212). At step 404 a determination is made whether the application(s) have performed their task(s). If the task(s) are not completed, the process flow returns to step 402 along the "No" branch of step 404. Otherwise, the task(s) are determined to be completed and the flow of processing moves along the "Yes" branch to step 406 where a determination whether to send a message regarding the completion of the task(s) performed is made. If no message is to be sent, then flow moves along "No" branch to step 408 where a determination whether to notify the user of the completion of the task(s) is made. If such notification is to be provided, then the user interface for the device (i.e., user interface 302) is updated at step 410. The updated status can also be demonstrated on any perceptible external interface (e.g., by illuminating an LED indicator). Otherwise the process terminates along the "No" branch of step 408. Returning to step 406, if a message is to be sent following completion of the task(s), then the relevant data is sent over the wireless network to any other implanted networked devices and/or external devices. The communication is performed using any protocol(s) necessary to establish communications. In one embodiment, the TCP/IP protocol is used to enable communication.

Figure 5:
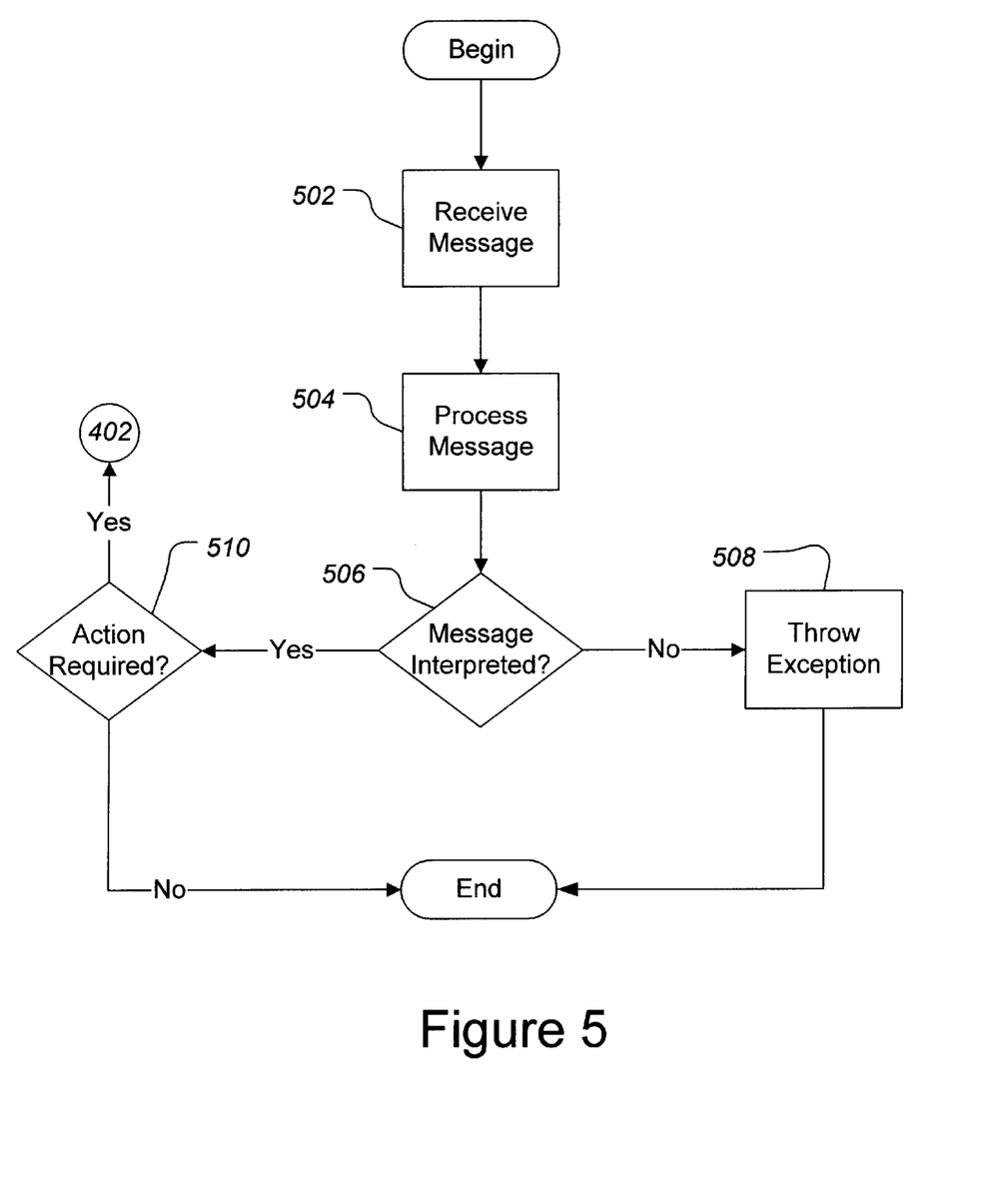
FIG. 5 is a flowchart illustrating the operation of a device configured to operate in a wireless network in accordance with one embodiment of the present invention.

One embodiment for processing messages is provided in FIG. 5. There, a message is received by an implanted device at step 502 using the device's external interface 214. The message is processed using the device's microprocessor, and a determination whether the message has been processed successfully is made at step 506. If the message cannot be processed, then the process flow proceeds along the "No" branch to step 508 where an exception is thrown and the process terminates. Otherwise, the process moves along the "Yes" branch of step 506 to step 510 at which a determination is made whether an action must be performed. If no action is to be performed, then the process terminates along "No" branch of step 510. Otherwise, the process flow moves along "Yes" branch of step 510 and the process flow moves to step 402 of FIG. 4.

Figure 6:
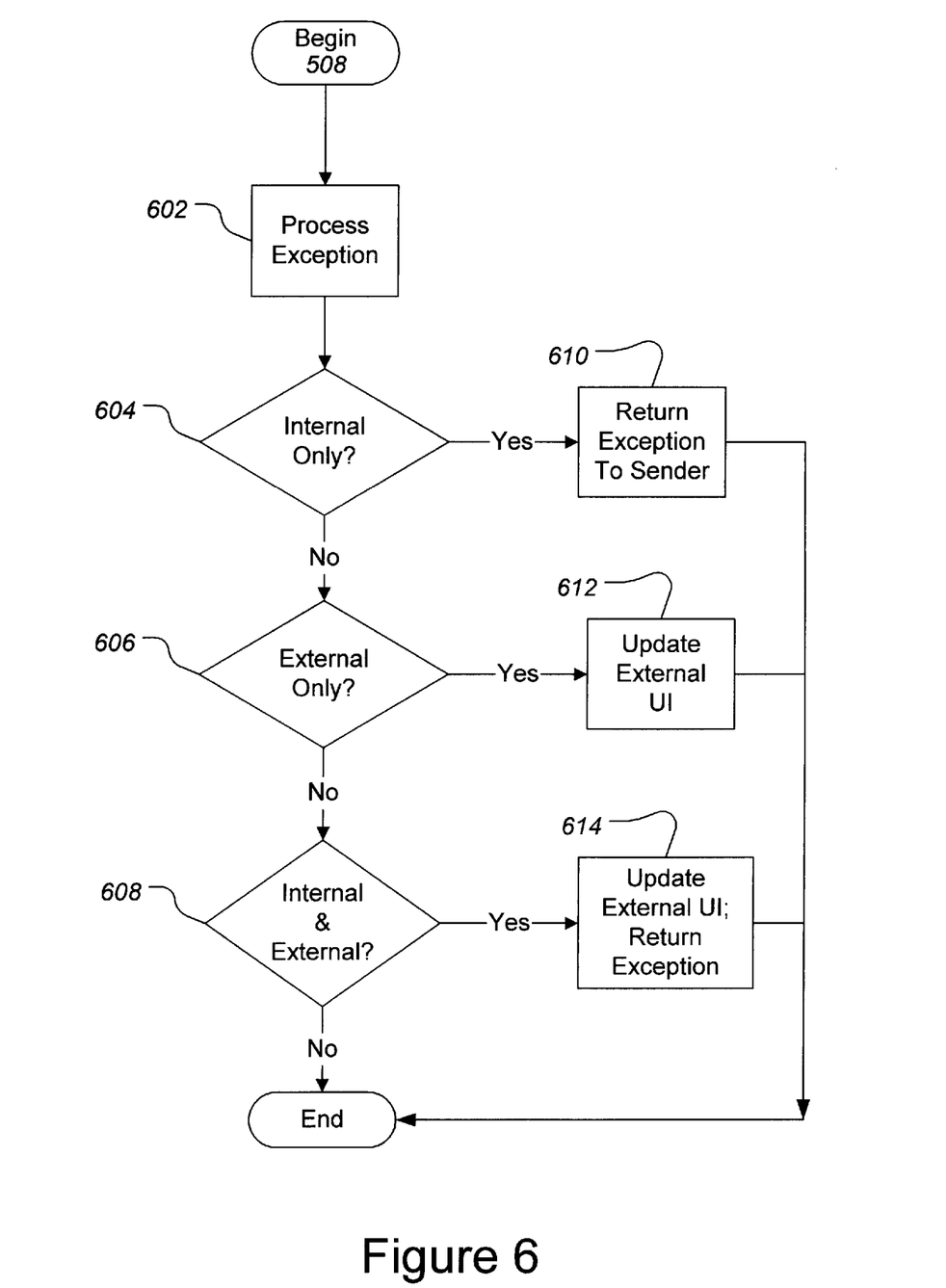
FIG. 6 is a flowchart illustrating the operation of step 508 in greater detail.

The process of step 508 is illustrated in greater detail in FIG. 6. There, the exception is processed at step 602. At step 604 a determination is made whether the exception is an "internal" exception only (i.e., one requiring a response to the sending device only). If the exception is not solely an internal exception, then the process moves along the "No" branch of step 604 to step 606 where a determination whether the exception is only an "external" exception (i.e., one requiring an external notification using a transdermal device). Otherwise, the process flow moves along the "Yes" branch of step 604 and an exception is sent to the sender at step 610 whereupon the process terminates. At step 606, if the process is solely an "external" exception, then the "Yes" branch of step 606 is followed, the external interface is updated at step 612, and the process terminates. Otherwise the process flow moves along the "No" branch of step 606 to step 608, where a determination is made whether the exception is both "internal" and "external". If so, then the process moves along the "Yes" branch to step 614 where the external user interface is updated and an exception is returned to the sender. Otherwise the "No" branch is followed, in which no exceptions are returned or interfaces updated, and the process terminates.

Figure 7:
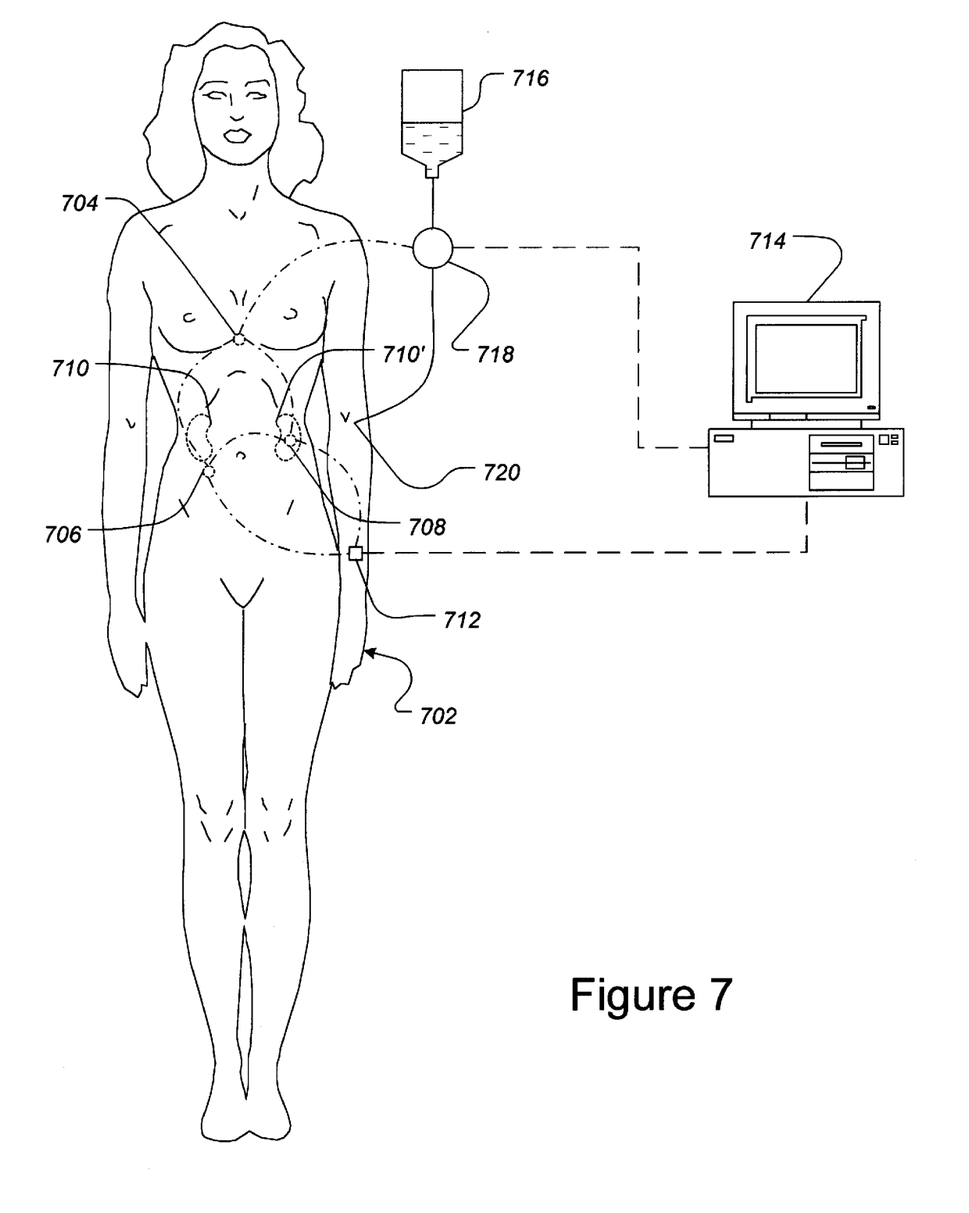
FIG. 7 illustrates a wireless network including implanted medical devices and sensors in addition to an external data processing/storage and pharmaceutical dispenser in accordance with one embodiment of the present invention.
Figure 8:
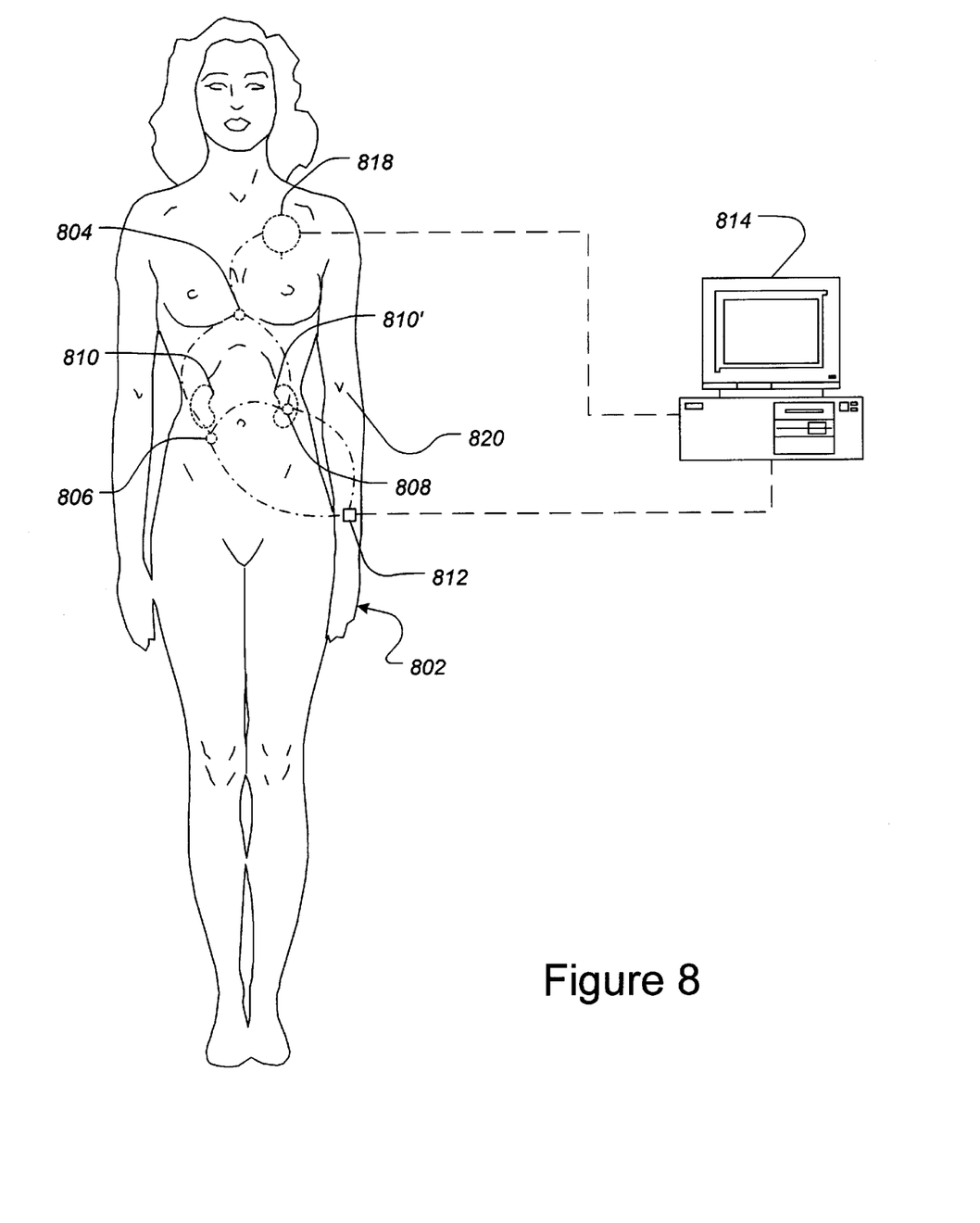
FIG. 8 illustrates a wireless network including implanted medical devices and sensors in addition to an internal pharmaceutical dispenser in accordance with one embodiment of the present invention.

FIGS. 7 and 8 illustrate two embodiments of the implementation of the networked implanted medical devices of the invention. In FIG. 7, a host 702 includes implanted subcutaneous implanted devices 704–708. Device 706 is located near left kidney 710 of host 702, and device 708 is located in right kidney 710'. Subcutaneous devices 704–708 perform various measurements (e.g., measurements related to renal function and/or renal cancer) and communicate the results of their determinations with each other and transdermal device 712. Device 712 can be configured to provide an externally visible warning to host 702 and/or caregivers (e.g., by illuminating an LED indicating an anomaly regarding renal finction). Devices 704–708 and 712 can optionally be further networked with a host computer 714 and/or a regulator 718 Regulator 718 is coupled with a reservoir 716 that controls the rate and/or total amount of medication released to host 702 as indicated by the intravenous line generally at 720.

Thus, in operation devices 704–708 include internal interfaces configured to determine various physiological parameters of host 702 related to renal function. Software running on these devices collects and processes the measurements and communicates these measurements across the network of devices 704–708, 712, and host computer 714 (also, optionally, with regulator 718). These measurements and associated calculations can be stored and/or further processed on host computer 714 and the amount of medication released to host 702 can be controlled based on such processes. Computer 714 can be further coupled with a wider network of computers to send information to other caregivers and/or databases, thus providing real-time information about the status of host 702 to remote caregivers in addition to a detailed history of the medical status of host 702.

FIG. 8 illustrates an alternate embodiment in which an internal medical device 818 is located within to host 802. Device 818 can be an internal medical dispenser or other device configured to produce a therapeutic effect in host 802. Examples of such devices are known in the bio-engineering arts (see, e.g., Ellinwood 1975; Thomassen 1991; Alt, Matula et al. 1994). As with FIG. 7, host 802 includes devices 804–808 having internal interfaces configured to determine various physiological parameters of host 802 related to renal function. Software running on these devices collects and processes the measurements and communicates these measurements across the network of devices 804–808, 812, and host computer 814 (also, optionally, with regulator 818). These measurements and associated calculations can be stored and/or further processed on host computer 814 and the amount of medication released to host 802 can be controlled based on such processes. Computer 814 can be fuirther coupled with a wider network of computers to send information to other caregivers and/or databases, thus providing real-time information about the status of host 802 to remote caregivers in addition to a detailed history of the medical status of host 802.

CONCLUSION

Thus, the present invention will be appreciated to provide networked, implanted medical devices. These devices can be used to monitor a patient's physiological state, monitor and/or control artificial organs and prosthetic devices, deliver medications, and provide physical stimuli to the patient. The devices and networks of the invention will be seen to provide greater flexibility, reliability, and responsiveness by allowing multiple devices having simpler, more specialized designs to work in concert to treat diseases or regulate body functions.

Although certain embodiments and examples have been used to describe the present invention, it will be apparent to those having skill in the art that various changes can be made to those embodiments and/or examples without departing from the scope or spirit of the present invention. For example, it will be appreciated from the foregoing that many steps of processing can be implemented in a sequence different from that described herein without altering the invention. In addition, various implanted devices not described herein explicitly can be used in conjunction with the present invention.

BIBLIOGRAPHY

The following references are incorporated herein by reference in their entirety and for all purposes.

Alt, E., M. Matula, et al. (1994). U.S. Pat. No. 5,342,404.
Barreras, F. J. S. and O. Jimenez (1998). U.S. Pat. No. 5,733,313.
Barreras, J. F. J. and R. Echarri (1998). U.S. Pat. No. 5,735,887.
Campione, M. and K. Walrath (1998). *The Java™ Tutorial Second Edition: Object-Oriented Programming for the Internet*. Reading, Massachusetts, Addison Wesley.
Crooks, R. M. and A. J. Ricco (1998). "New Organic Materials Suitable for Use in Chemical Sensor Arrays." *Acc. Chem. Res.* 31: 219–227.
Ellinwood, E. H. (1975). U.S. Pat. No. 3,923,060.
Genest, L. J. (1985). U.S. Pat. No. 4,531,526.
Herzog, J. H. (1996). *Design and Organization of Computing Structures,* Franklin, Beedle & Associates, Inc.
Hogen Esch, J. H. L. (1994). U.S. Pat. No. 5,372,133.
Lauks, I. R. (1998). "Microfabricated Biosensors and Microanalytical Systems for Blood Analysis." *Acc. Chem. Res.* 31: 317–324.
Martin, J. and K. K. Chapman (1989). *Local Area Networks: Architectures and Implementations,* Prentice Hall.
Mitrovics, J., H. Ulmer, et al. (1998). "Modular Sensor Systems for Gas Sensing and and Odor Monitoring: The MOSES Concept." *Acc. Chem. Res.* 31: 307–315.
Morgan, W. A. and T. W. Richards (1995). U.S. Pat. No. 5,476,488.
Myllymäki, M. (1997). U.S. Pat. No. 5,670,944.
Nappholz, T. A., W. N. Hursta, et al. (1992). U.S. Pat. No. 5,113,869.
Pollack, P. (1989). U.S. Pat. No. 4,854,328.
Prutchi, D. and P. J. Paul (1998). U.S. Pat. No. 5,730,125.
Ralston, A. and E. D. Reilly (1993). *Encyclopedia of Computer Science,* Van Norstrand Reinhold.

Semancik, S. and R. Cavicchi (1998). "Kinetically Controlled Chemical Sensing Using Micromachined Structures." *Acc. Chem. Res.* 31: 279–287.

Snell, J. D. (1998). U.S. Pat. No. 5,270,771.

Snell, J. D. and T. G. Levin (1998). U.S. Pat. No. 5,724,985.

Stone, H. S. (1983). *Microcomputer Interfacing,* Addison Wesley.

Thomassen, N. (1991). U.S. Pat. No. 4,996,986.

Walt, D. R. (1998). "Fiber Optic Imaging Sensors." *Acc. Chem. Res.* 31: 267–278.

Zurbrügg, H. R. (1996). U.S. Pat. No. 5,522,394.

What is claimed:

1. A network device configured to be implanted in a subject and communicate over a computer network, said implantable network device comprising:
    an internal interface in physiological communication with said subject, said internal interface being coupled with, and configured to send signals to;
    a processor, said processor being configured to receive signals from said internal interface and process said signals, and said processor further being configured to send and receive signals over a computer network from another said network device implanted in said subject, said processor being further coupled with;
    a computer memory for storing data and instructions for said processor, and an external interface for sending and receiving signals over a computer network, and a power source.

2. The device of claim 1, wherein said internal interface comprises a sensor.

3. The device of claim 2, wherein said sensor comprises an antibody detection component.

4. The device of claim 3, wherein said antibody detection component includes antibodies directed to tumor-specific antigens.

5. The device of claim 3, wherein said antibody detection component includes antibodies directed to at least one virus or viral product.

6. The device of claim 3, wherein said antibody detection component includes antibodies directed to at least one bacterium or bacterial product.

7. The device of claim 3, wherein said antibody detection component includes antibodies directed to at least one metabolite of said subject.

8. The device of claim 2, wherein said sensor is configured to measure a physiological parameter of said subject.

9. The device of claim 8, wherein said physiological parameter is selected from the group consisting of heart rate, blood oxygen concentration, blood flow rate, temperature, and blood pH.

10. The device of claim 1, wherein said implantable device is configured to be implanted in said subject subcutaneously.

11. The device of claim 1, wherein said implantable device is configured to be implanted in said subject transdermally, and said external interface comprises an external signal that is perceptible by said subject.

12. The device of claim 11, wherein said external interface is configured to communicate with a source external to said subject.

13. The device of claim 1, wherein said external interface is configured to communicate with a source external to said subject.

14. The device of claim 13, wherein said source is a communications network.

15. A computer network, comprising a plurality of network devices as described in claim 1 implanted in a subject, said network devices being configured to send and receive signals among themselves.

16. The implantable computer network of claim 15, wherein said implantable network devices are further configured to send and receive signals from a source external to said subject.

17. The device of claim 16, wherein said source comprises an external computer network.

18. A method of monitoring the physiological condition of a subject, comprising the steps of:
    implanting an implantable network device as described in claim 1 in said subject;
    establishing communication with said implantable network device;
    determining at least one physiological parameter using said implantable network device; and
    communicating said measured parameter using said implantable network device over a computer network.

19. The method of claim 18, wherein said step of communicating over a computer network includes sending a signal to a second implantable network device.

20. The method of claim 18, wherein said step of communicating over a computer network includes sending a signal to an external receiver.

21. The method of 19, including the step of receiving said signal by said second implantable network device.

22. The method of claim 21, including the step of dispensing a therapeutic substance to said subject under the computer control of said second implantable network device in response to receiving said signal.

23. The method of claim 18, further including the step of updating a user interface over said computer network.

24. The method of claim 18, further including the steps of:
    determining whether a signal should be sent to a second network device in communication with said first implantable network device across a computer network; and
    sending a signal to said second implantable network device across said computer network in response to a determination that said signal should be sent.

25. The method of 24, further including the step of determining whether a user interface in communication with said first implantable network device should be updated, and updating said user interface in response to a determination that said user interface should be updated.

26. The method of claim 18, fuirther including the steps of:
    receiving a signal from a networked device;
    processing said signal and determining whether said signal is interpretable;
    determining whether an action is required to be taken if said signal is interpretable; and
    taking said action in response to a determination that an action is required to be taken.

27. The method of claim 26, further including the step of throwing an exception in response to determining that said signal cannot be interpreted.

28. The method of claim 27, wherein said step of throwing an exception comprises the sub-steps of:
    determining whether said exception is internal, and sending said exception to said first implantable network device if said exception is internal;
    determining whether said exception is external, and sending said exception to a user interface if said exception is external; and
    sending said exception to both said first implantable network device and said user interface if said exception is both internal and external.

* * * * *

UNITED STATES PATENT AND TRADEMARK OFFICE
CERTIFICATE OF CORRECTION

PATENT NO.    : 6,358,202 B1  
DATED         : March 19, 2002  
INVENTOR(S)   : Michael Arent Page 1 of 1

It is certified that error appears in the above-identified patent and that said Letters Patent is hereby corrected as shown below:

Column 7,
Line 31, please change "finction" to -- function --.

Column 8,
Line 3, please change "fuirther" to -- further --.

Column 10,
Line 43, please change "fuirther" to -- further --.

Signed and Sealed this

Eighteenth Day of February, 2003

JAMES E. ROGAN
*Director of the United States Patent and Trademark Office*